US010500258B2

(12) United States Patent
Li et al.

(10) Patent No.: US 10,500,258 B2
(45) Date of Patent: *Dec. 10, 2019

(54) DNA VACCINES AND METHODS FOR THE PREVENTION OF TRANSPLANTATION REJECTION

(71) Applicant: LOMA LINDA UNIVERSITY, Loma Linda, CA (US)

(72) Inventors: Fengchun Li, Loma Linda, CA (US); Alan P. Escher, Redlands, CA (US)

(73) Assignee: Loma Linda University, Loma Linda, CA (US)

( * ) Notice: Subject to any disclaimer, the term of this patent is extended or adjusted under 35 U.S.C. 154(b) by 316 days.

This patent is subject to a terminal disclaimer.

(21) Appl. No.: 15/172,937

(22) Filed: Jun. 3, 2016

(65) Prior Publication Data

US 2017/0028039 A1  Feb. 2, 2017

Related U.S. Application Data

(60) Continuation of application No. 13/543,567, filed on Jul. 6, 2012, now Pat. No. 9,358,277, which is a
(Continued)

(51) Int. Cl.
*A61K 39/00* (2006.01)
*A61K 9/00* (2006.01)
*A61K 45/06* (2006.01)

(52) U.S. Cl.
CPC .......... *A61K 39/001* (2013.01); *A61K 9/0019* (2013.01); *A61K 45/06* (2013.01);
(Continued)

(58) Field of Classification Search
CPC ................................... A61K 39/001
See application file for complete search history.

(56) References Cited

U.S. PATENT DOCUMENTS

| 6,410,273 B1 | 6/2002 | Crouzet et al. |
| 2003/0176378 A1 | 9/2003 | Weiner et al. |

(Continued)

FOREIGN PATENT DOCUMENTS

| WO | 99/44644 | 9/1999 |
| WO | 00/59538 | 10/2000 |

(Continued)

OTHER PUBLICATIONS

Eisenberg R. (2005, Eur. J. Immunology, vol. 35, pp. 367-370) (Year: 2005).*

(Continued)

*Primary Examiner* — Thaian N Ton
*Assistant Examiner* — David A. Montanari
(74) *Attorney, Agent, or Firm* — Seed IP Law Group LLP

(57) ABSTRACT

Methods for preventing, delaying the onset of, or treating rejection of an allograft using a DNA vaccine, where the vaccine can comprise a polynucleotide encoding a pro-apoptotic protein, like BAX and/or a polynucleotide encoding an autoantigen or donor antigen, like secreted glutamic acid decarboxylase 55. Administering one of the DNA vaccines to a transplant recipient, as described herein, can induce a donor specific tolerogenic response.

16 Claims, 6 Drawing Sheets

Specification includes a Sequence Listing.

Related U.S. Application Data division of application No. 12/409,351, filed on Mar. 23, 2009, now abandoned, which is a continuation of application No. PCT/US2009/037027, filed on Mar. 12, 2009, and a continuation-in-part of application No. 11/913,657, filed as application No. PCT/US2006/017763 on May 5, 2006, now Pat. No. 8,778,327.

(60) Provisional application No. 61/036,004, filed on Mar. 12, 2008, provisional application No. 60/680,249, filed on May 11, 2005.

(52) U.S. Cl.
CPC .... *A61K 2039/53* (2013.01); *A61K 2039/545* (2013.01); *A61K 2039/55516* (2013.01); *A61K 2039/55561* (2013.01); *A61K 2039/577* (2013.01)

(56) References Cited

U.S. PATENT DOCUMENTS

| | | |
|---|---|---|
| 2006/0153842 A1 | 7/2006 | Lake et al. |
| 2008/0194510 A1 | 8/2008 | Escher et al. |
| 2010/0068813 A1 | 3/2010 | Li et al. |
| 2012/0308577 A1 | 12/2012 | Li et al. |

FOREIGN PATENT DOCUMENTS

| | | |
|---|---|---|
| WO | 2004/034966 | 4/2004 |
| WO | 2006/124375 A2 | 11/2006 |

OTHER PUBLICATIONS

Delavallee et al. 2008, Annals of Med., vol. 40, pp. 343-351. (Year: 2008).*
Xavier-Elsas, 2007, Clinical and Experimental Allergy, vol. 37, pp. 29-38 (Year: 2007).*
Friedman et al., 2012, Liver Transplantation, vol. 18(2), pp. 166-176 (Year: 2012).*
Harrison LC, 2005, Human Vaccines, vol. 1, pp. 143-150 (Year: 2005).*
Garcia et al. (2012, J. Transplantation, Article ID 842141, pp. 1-7) (Year: 2012).*
Adamus et al., "Autoimmunity against Carbonic Anhydrase II Affects Retinal Cell Functions in Autoimmune Retinopathy,"*J. Autoimmun.* 32(2):133-139 (2009).
Balasa et al., "Vaccination with glutamic acid decarboxylase plasmid DNA protects mice from spontaneous autoimmune diabetes and B7/CD28 costimulation circumvents that protection," *Clin. Immunol.* 99(2): 241-252 (2001).
Belakova et al., "DNA vaccines: are they still just a powerful tool for the future?" *Arch Immunol Ther Exp (Warsz)* 55(6):387-98 (2007).
Borner et al., "The protein bcl-2 alpha does not require membrane attachment, but two conserved domains to suppress apoptosis," J Cell Biol. 126(4):1059-1068 (1994).
Bros et al., "A newly established murine immature dendritic cell line can be differentiated into a mature state, but exerts tolerogenic function upon maturation in the presence of glucocorticoid," *Blood* 109:3820-2829 (2007).
Bumgardner et al., "Unusual patterns of alloimmunity evoked by allogeneic liver parenchymal cells," *Immunol Rev.* 174: 260-279 (2000).
Chao et al., "BCL-2 family: regulators of cell death," *Annu. Rev. Immunol.* 16:395-419 (1998).
Chattergoon, M. A., et al., "Targeted antigen delivery to antigen-presenting cells, including dendritic cells by engineered Fas-mediated apoptosis," *Nat. Biotechnol.* 9:974-797 (2000).
Chernysheva et al., "T cell proliferation induced by autologous non-T cells is a response to apoptotic cells processed by dendritic cells," *J Immunol.* 169(3):1241-1250 (2002).
Contreras et al., "Gene transfer of the Bcl-2 gene confers cytoprotection to isolated adult porcine pancreatic islets exposed to xenoreactive antibodies and complement," *Surgery* 130(2):166-174 (Aug. 2001).
Contreras et al., "Cytoprotection of pancreatic islets before and early after transplantation using gene therapy," *Kidney International* 61(1 Suppl.):79-84 (Jan. 2002).
Elnekave et al., "Intradermal naked plasmid DNA immunization: mechanisms of action," *Expert Rev. Vaccines* 10(8):1169-1182 (2011).
Efrat et al., "Adenovirus Early Region 3 (E3) Immunomodulatory Genes Decrease the Incidence of Autoimmune Diabetes in NOD Mice," *Diabetes* 50(5):980-984 (May 2001).
Erickson et al., "Expression of carbonic anhydrase II (CA II) promoter-reporter fusion genes in multiple tissues of transenic mice does not replicate normal patterns of expression indicating complexity of CA II regulation in vivo," *Biochem Genet.* 33(11-12):421-437 (1995).
Filippova et al., "Effects of Plasmid DNA Injection on Cyclophosphamide-Accelerated Diabetes in NOD Mice," *DNA and Cell Biology* 20(3):175-181 (Mar. 2001).
Guenette et al. "DNA methylation inhibits transcription of procollagen α2(1) promoters," *Biochem. Journal* 283:699-703 (1992).
Hedstrand et al., "The Transcription Factors SOX9 and SOX10 are Vitiligo Autoantigens in Autoimmune Polyendocrine Syndrome Type I," *The Journal of Biological Chemistry* 276(38):35390-35395 (2001).
Horner et al., "Skin tolerance: in search of the Holy Grail," *European Society for Organ Transplantation* 21:101-112 (2008).
Hosoda et al., "Detection of autoantibody against carbonic anhydrase II in various liver diseases by enzyme-linked immunosorbent assay using appropriate conditions," *Clinica Chimica Acta* 342:71-81 (2004).
Hu et al., "Cell Apoptosis and Message Transduction," see "Molecular Medicine of Apoptosis," Military Medical Science Press, Beijing, Chapter 6, pp. 93-101 (no translation is available for this reference).
Huurman et al., "Cellular Islet Autoimmunity Associates with Clinical Outcome of Islet Cell Transplantation," *PLoS One* 3(6):e2435 (2008).
Igata et al., "Molecular cloning and functional analysis of the murine bax gene promoter," *Gene* 238(2):407-15 (1999).
Ilan et al., "Insertion of the adenoviral E3 region into a recombinant viral vector prevents antiviral humoral and cellular immune responses and permits long-term gene expression," *Proc. Natl. Acad. Sci. USA* 94:2587-2592 (Mar. 1997).
Iwata et al., "Anti-Type V Collagen Humoral Immunity in Lung Transplant Primary Graft Dysfunction," *Journal of Immunology* 181(8):5738-5747 (2008).
Kagawa et al., "A binary adenoviral vector system for expressing high levels of the proapoptotic gene bax," *Gene Therapy* 7:75-79 (2000).
Kerkar et al., "Cytochrome P4502D6 193-212: A New Immunodominant Epitope and Target of Virus/Self Cross-Reactivity in Liver Kidney Microsomal Autoantibody Type 1-Positive Liver Disease," *Journal of Immunology* 170:1481-1489 (2003).
Klinman et al., "Use of CpG oligodeoxynucleotides as immune adjuvants," *Imm. Rev.* 1999:201-216 (2004).
Klinman et al., "Contribution of CpG motifs to the immunogenicity of DNA vaccines," *Journal of Immunology* 158:3635-3639 (2007).
Komura et al., "Repression of transient expression by DNA methylation in transcribed regions of reporter genes introduced into cultured human cells," *Biochimica et Biophysica Acta* 1260:73-78 (1995).
Krieg, "The role of CpG motifs in innate immunity," *Curr. Opin. Immun.* 12:35-43 (2000).
Li et al., "Intradermal or oral delivery of GAD-encoding genetic vaccines suppresses type 1 diabetes," *DNA and Cell Biology* 22(4):227-232 (2003).
Li et al., "Co-delivery of pro-apoptotic BAX with a DNA vaccine recruits dendritic cells and promotes efficacy of autoimmune diabetes prevention in mice," *Vaccine* 22:1751-1763 (2004).

(56) References Cited

OTHER PUBLICATIONS

Li et al., "Pro-apoptotic DNA vaccination ameliorates new onset of autoimmune diabetes in NOD mice and induces foxp3+ regulatory T cells in vitro," *Vaccine* 24:5036-5046 (2006).
Li et al., "A therapeutic DNA vaccination strategy for autoimmunity and transplantation," *Vaccine* 28:1897-1904 (2010).
Li et al., "DNA vaccines for transplantation," *Expert Opin. Biol. Ther.* 10(6):903-915 (2010).
Li et al., "Decreased insulitis and blood blucose levels after injection of GAD-transduced lymphocytes into NOD mice," *Mol. Ther.* 6(6):701-709 (2002).
Lim et al., "Cutting Edge: Direct Suppression of B Cells by CD4+CD25+ Regulatory T Cells," *Journal of Immunology* 175:4180-4183 (2005).
Martin et al., "Cell to cell interaction in the immune system," *Journal of Experimental Medicine* 128:855-874 (1968).
Mathisen et al., "Gene Therapy in Experimental autoimmune Encephalomyelitis," *J. Clin. Immunol.* 20(5):327-333 (2000).
McCluskie et al., "Route and method of delivery of DNA vaccine influence immune responses in mice and non-human primates," *Mol. Med.* 5:287-300 (1999).
McGowan et al., "Characterization of the rat carbonic anhydrase II gene structure: Sequence analysis of the 5' flanking region and 3' UTR," *Gene* 186(2): 181-188 (1997).
Meinck et al., "Antibodies against glutamic acid decarboxylase: prevalence in neurological diseases," *J. Neurol Neurosur Psychiatry* 71:100-103 (2001).
Miranda et al., "DNA Methylation: The Nuts and Bolts of Repression," *J. Cell. Physiol.* 213:384-390 (2007).
Nakao et al., "Regulation of transcription and chromatin by methyl-CpG binding protein MBD1," *Brain Dev.* 23(Suppl 1):S174-6 (2001).
Ono et al., "Carbonic Anhydrase in the Membrane of the Endoplasmic Reticulum of Male Rat Liver," *Proc. Natl. Acad. Sci.* 89:11721-11725 (Dec. 1992).
Pasquini et al., "The Effect of CpG Sequences on the B Cell Response to a Viral Glycoprotein Encoded by a Plasmid Vector," *Gene Therapy* 6(8):1448-1455 (Aug. 1, 1999).
Peters et al., "The Mouse as a model for human biology: a resource guide for complex trait analysis," *Nature Reviews* 8:58-69 (Jan. 2007).
Pierce et al., "Adenovirus Early Region 3 Antiapoptotic 10.4K, 14.5K, and 14.7K Genes Decrease the Incidence of Autoimmune Diabetes in NOD Mice," *Diabetes* 52:1119-1127 (May 2003).
Qu et al., "Demethylation and expression of methylated plasmid DNA stably transfected into HeLa cells," *Nucleic Acids Research* 27(11):2332-2338 (1999).
Rabinovitch et al., "Transfection of Human Pancreatic Islets With an Anti-Apoptotic Gene (bdl-2) Protects B-Cells From Cytokine-Induced Destruction," *Diabetes* 48(6):1223-1229 (Jun. 1999).
Razin, "CpG Methylation, Chromatin Structure and Gene Silencing—a Three-Way Connection," *The EMBO Journal* 17(17):4905-4908 (1998).
Reindl et al., "Antibodies Against the Myelin Oligodendrcyte Glycoprotein and the Myelin Basic Protein in Multiple Sclerosis and Other Neurological Diseases: A Comparative Study," *Brain* 122:2047-2056 (2001).
Restifo "Building better vaccines: how apoptotic cell death can induce inflammation and activate innate and adaptive immunity," *Curr. Opin. Immunol.* 12(5) (2000).
Reyes-Sandoval, et al., "CpG methylation of a plasmid vector results in extended transgene product expression by circumventing induction of immune responses," *Molecular Therapy* 9(2): 249-261 (2004).
Sasaki et al., "Apoptosis-mediated enhancement of DNA-raised immune responses by mutant caspases," *Nat. Biotechnol.* 19(6):543-547 (2001).
Scheerlink et al., "Genetic adjuvants for DNA vaccines," *Vaccine* 19(17-19):2647-2656 (2001).
Schowalter et al., "Heterologous Expression of Adenovirus E3-gp19K in an Ela-Deleted Adenovirus Vector Inhibits MHC I Expression in Vitro, But Does Not Prolong Transgene Expression in Vivo," *Gene Therapy* 4:351-360 (1997).
Scheule, "The role of CpG motifs in immunostimulation and gene therapy," *Advs. Drug Delivery Rev.* 44119-134 (2000).
Seetharam et al., "Alloimmunity and Autoimmunity in Chronic Rejection," *Curr Opin Organ Transplant* 15(4):531-536 (2010).
Simone et al., "Immunologic Vaccination for the Prevention of Autoimmune Diabetes (Type 1A)," *Diabetes Care* 22(Suppl. 2):B7-B15 (Mar. 1999).
Steinman et al., "The Induction of Tolerance by Dendritic Cells That Have Captured Apoptotic Cells," *J. Exp. Med.* 191(3):411-416 (2000).
Szabo et al., "Structure and the promoter region of the mouse gene encoding the 67-kD form of glutamic acid decarboxylase," *DNA Cell Biol.* 15(12):1081-91 (1996).
Taniguchi et al., "High Prevalence of Autoantibodies Against Carbonic Anhydrase II and Lactoferrin in Type 1 Diabetes: Concept of Autoimmune Exocrinopathy and Endocrinopathy of the Pancreas," *Pancreas* 27(1): 26-30 (2003).
Tisch et al. "Antigen-specific mediated suppression of beta cell autoimmunity by plasmid DNA vaccination," *Journal of Immunology* 166(3):2122-2132 (2001).
Tokui et al., "Studies on prevention of diabetes in NOD mice by intramuscular administration of plasmid GAD and IL-4," *American Chemical Society* 25(125):1148 (1996).
Trucco et al., "Gene Therapy Strategies to Prevent Autoimmune Disorders," *Current Gene Therapy* 2:341-354 (2002).
Ulmer et al., "Gene-based vaccines: recent technical and clinical advances," *Trends Mol Med.* 125:216-22 (2006).
Wallet et al., "MerTK is required for apoptotic cell—induced T cell tolerance," *J. Exp. Med.* 205(1): 219-232 (2008).
Watson et al., "Pruning of Alloreactive CD4+ T Cells Using 5-(and 6) Carboxyfluorescein Diacetate Succinimidyl Ester Prolongs Skin Allograft Survival," *The Journal of Immunology* 173:6574-6582 (2004).
Yamaguchi et al., "The Effect of Pretreatment with Class I Major Histocompatibility Complex (MHC) Antigens on Hepatic or Cardiac Allograft Survival in the Rat," *Transplant Proc.* 21(3):3355 (Jun. 1989).
Zardo et al., "Dynamic and reversibility of heterochromatic gene silencing in human disease," *Cell Research* 15(9):679-90 (2005).
Andrés, "Cancer incidence after immunosuppressive treatment following kidney transplantation," *Critical Reviews in Oncology/Hematology* 56:71-85, 2005.
Li et al., "DNA Vaccination for Type 1 Diabetes Prolongs Skin Allograft Survival in a Donor-Specific Manner," *Clinical Immunology* 131:S76, 2009.
Shabahang et al., "Recent Patents on Immunoregulatory DNA Vaccines for Autoimmune Diseases and Allograft Rejection," *Recent Patents on DNA and Gene Sequences* 4:122-131, 2010.
Valujskikh et al., "Development of Autoimmunity After Skin Graft Rejection via an Indirect Alloresponse," *Transplantation* 73(7):1130-1137, 2002.
Yu et al., "Advances in transplantation tolerance," *The Lancet* 357:1959-1963, 2001.

\* cited by examiner

DNA VACCINES AND METHODS FOR THE PREVENTION OF TRANSPLANTATION REJECTION

BACKGROUND

Prevention of organ rejection in the clinic presently relies on administration of cocktails of immunosuppressants (Tacrolimus, Rapamycin, MMF, AZA, corticosteroids). The drugs are efficient for prevention of acute rejection, but do not prevent chronic rejection. In addition, because these drugs interfere with immune responses non-specifically, their chronic use exposes patients to high risks of cancer and infection. Other approaches that are being tested are co-stimulatory blockade and bone-marrow chimerism. However, "late-onset chronic rejection, as well as the toxicity of some of these regimens, remain as significant limitations that hamper clinical application" (Ochiai et al., *Front. Biosci.* 2007, 12:4248-53).

SUMMARY

One embodiment of the present invention comprises a method for preventing, delaying the onset of, or treating rejection of an allograft or an allogeneic transplant. The method comprises: (A) selecting a recipient in need of a graft or transplant and an allograft or allogeneic transplant donor; (B) grafting tissue or transplanting a solid organ from the donor to the recipient; and (C) administering to the recipient one or more than one dose of a DNA vaccine. The DNA vaccine is selected from the group consisting of: three individual plasmids and a two plasmid vaccine. The first plasmid comprises (a) a polynucleotide encoding a pro-apoptotic protein; and (b) a promoter controlling the expression of the polynucleotide encoding the pro-apoptotic protein. The second plasmid comprises: (a) a polynucleotide sequence encoding an autoantigen or donor antigen; (b) a promoter controlling expression of the polynucleotide sequence encoding the autoantigen or donor antigen; and (c) a plurality of CpG motifs, where the CpG motifs are methylated sufficiently to diminish the recipient's immune response to unmethylated CpG motifs. The third plasmid comprises: (a) a polynucleotide sequence encoding an autoantigen or donor antigen; (b) a promoter controlling expression of the polynucleotide sequence encoding the autoantigen or donor antigen; (c) a polynucleotide encoding a pro-apoptotic protein; (d) a promoter controlling expression of the polynucleotide encoding the pro-apoptotic protein; and (e) a plurality of CpG motifs, where the CpG motifs are methylated sufficiently to diminish the recipient's immune response to unmethylated CpG motifs. The two plasmid vaccine comprises a combination of the first plasmid and the second plasmid.

In some embodiments of the present invention, the engrafted tissues or transplanted organs are selected from the group consisting of skin grafts, islet cell transplants, and partial or whole organ transplants. In additional embodiments of the method, the partial or whole organ transplants are selected from the group consisting of hearts, lungs, kidneys and livers.

In one embodiment of the method, the DNA vaccine is one or more than one plasmid comprising a plurality of methylated CpG motifs, where the one or more than one plasmid is resistant to digestion by the restriction enzyme HpaII. In a preferred embodiment, the DNA vaccine is one or more than one plasmid comprising a plurality of CpG motifs, where the CpG motifs of one or more than one plasmid are methylated by SssI methylase.

In one embodiment of the present invention, the promoter capable of expressing the polynucleotide encoding the autoantigen or the donor antigen, or the promoter capable of expressing the polynucleotide encoding the pro-apoptotic protein, or both the promoter capable of expressing the polynucleotide encoding the autoantigen or the donor antigen, and the promoter capable of expressing the polynucleotide encoding the pro-apoptotic protein maintain their promoter function after methylation.

In another embodiment of the present method, the third plasmid further comprises an internal ribosome entry site (IRES) sequence, where the IRES sequence is SEQ ID NO:3 from the EMC virus, to permit translation of the polynucleotide encoding the autoantigen or the donor antigen, and the polynucleotide encoding the pro-apoptotic protein from the same transcript.

In one embodiment of the present invention, the DNA vaccine comprises the first plasmid and the second plasmid in a ratio of between 1/1000 to 1000/1. In a preferred embodiment, the DNA vaccine comprises the first plasmid and the second plasmid in a ratio of between 1/100 to 100/1. In a particularly preferred embodiment, the DNA vaccine comprises the first plasmid and the second plasmid in a ratio of between 1/10 to 10/1.

In specific embodiments of the present invention, the autoantigen or donor antigen 1s selected from the group consisting of carbonic anhydrase II, collagen, CYP2D6 (cytochrome P450, family 2, subfamily Device 400, polypeptide 6), glutamic acid decarboxylase, secreted glutamic acid decarboxylase 55, SEQ ID NO:1, insulin, myelin basic protein and SOX-10 (SRY-box containing gene 10) or any relevant autoantigen that is present in both the transplant recipient and the donor allograft.

In additional specific embodiments, the pro-apoptotic protein is selected from the group consisting of BAX, SEQ ID NO:2, a modified caspase, Tumor Necrosis Factor Receptor, Death Receptor 3 (DR3), Death Receptor 4 (DR4), Death Receptor 5 (DR5) and a FAS receptor.

In one embodiment of the method, the DNA vaccine is administered in an effective dose, wherein an effective dose is an amount sufficient to prevent, delay the onset, or treat rejection of an allograft or an allogeneic transplant by the recipient.

In another embodiment of the method, the DNA vaccine is administered in an effective dose, wherein an effective dose is an amount sufficient to induce a donor-specific tolerogenic response.

In preferred embodiments, the DNA vaccine is (a) administered in a plurality of doses; (b) the dose of the DNA vaccine is about 0.001 mg/Kg of body weight of the recipient to about 100 mg/Kg of body weight of the recipient; and/or (c) the dose is administered weekly between two times and 100 times.

In some embodiments the DNA vaccine is administered by an epidermal, intradermal, intramuscular, intranasal, intravenous, intraperitoneal or oral route. In a preferred embodiment, the DNA vaccine is administered by an injection proximal to the site of the allograft or allogeneic transplant.

In one embodiment, the method further comprises the step of administering a dose of one or more than one immunosuppressant agent before, on the day of and/or after engraftment or transplantation. As will be appreciated by one of skill in the art, with reference to the present disclosure, the dose of one or more than one immunosuppressant agent can be administered simultaneously, separately or sequentially.

In specific embodiments, the one or more than one immunosuppressant agent is selected from the group consisting of corticosteroids, glucocorticoids. cyclophosphamide, 6-mercaptopurine, azathioprine, methotrexate cyclosporine, mycophenolate mofetil, mycophenolic acid, tacrolimus, sirolimus, everolimus, mizoribine, leflunomide, deoxyspergualin, brequinar, azodicarbonamide, vitamin D analogs, antilymphocyte globulin, antithymocyte globulin, anti-CD3 monoclonal antibodies, anti-interleukin-2 receptor (anti-CD25) antibodies, anti-CD52 antibodies, anti-CD20 antibodies, anti-tumor necrosis factor reagents and LFA-1 inhibitors.

In a preferred embodiment, the method includes the step of administering a single dose of antilymphocyte globulin, at a dosage of about 1.6 mg/20 g of body weight, on the day of engraftment or transplantation.

In another preferred embodiment, the method includes the step of administering rapamycin at a dosage of from 0.05 to 15 mg/day.

One embodiment of the present invention provides a method for preventing, delaying the onset of or treating rejection of an allograft or an allogeneic transplant, comprising the steps of: (A) selecting a graft or transplant recipient and an allograft or allogeneic transplant donor; (B) grafting tissue or transplanting a solid organ from the donor to the recipient; and (C) inducing a donor-specific immune response that elevates regulatory T cell activity by administering to the recipient one or more than one dose of a DNA vaccine comprising a first plasmid and a second plasmid. The first plasmid comprises: (a) a polynucleotide encoding a pro-apoptotic protein; and (b) a promoter controlling the expression of the polynucleotide encoding the pro-apoptotic protein. The second plasmid comprises: (a) a polynucleotide sequence encoding an autoantigen or donor antigen; (b) a promoter controlling expression of the polynucleotide sequence encoding the autoantigen or donor antigen; and (c) a plurality of CpG motifs, where the CpG motifs are methylated sufficiently to diminish the recipient's immune response to unmethylated CpG motifs.

In one version of this embodiment, administration of the plasmids elevates expression of IL-4 (interleukin 4). In another version of this embodiment, administration of the plasmids further induces a donor-specific tolerogenic response. In yet another version of this embodiment, administration of the plasmids elevates expression of inhibitory Fc receptor, FcγIIb, and Il-1ra. In still another version of this embodiment, administration of the plasmids reduces an autoimmune response. In an alternative version of this embodiment, administration of the plasmids reduces expression of Tnfα (tumor necrosis factor) and Ifnγ (gamma interferon). As will be appreciated by one of skill in the art with reference to the present disclosure, alternative versions of the method can include alternative steps where the first plasmid and the second plasmid are administered simultaneously or sequentially.

BRIEF DESCRIPTION OF THE DRAWINGS

These features, aspects and advantages of the present invention will become better understood with regard to the following description, appended claims and accompanying drawings where:

FIGS. 2A and 2B show allograft survival after immunization with non-methylated and methylated vaccines, respectively. #, P<0.003 compared to vector and IS alone (Mann-Whitney), @, P<0.005 compared to methylated vector (Mvector) and IS alone, ♦, P<0.04 compared to sGAD in A, ★, P<0.04 compared to methylated, non-methylated vector controls and IS alone (Kaplan-Meier).

In FIGS. 3A and 3B, @, P<0.05 compared to control. In FIG. 3 C, #, @, P<0.05 compared to cells stimulated with self and third-party antigens, respectively.

DETAILED DESCRIPTION

Figure 1:
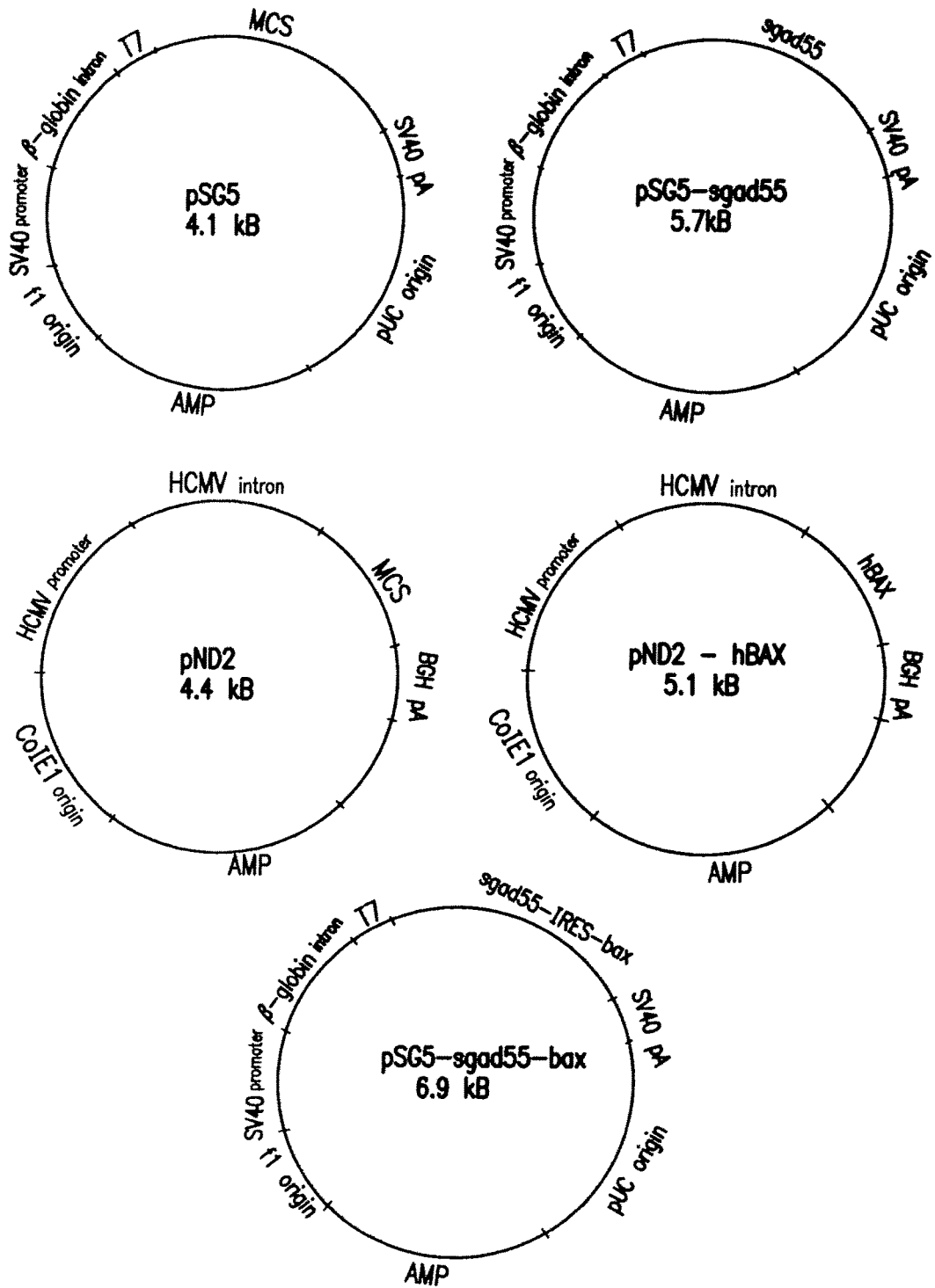
FIG. 1 shows schematic depictions of the plasmids disclosed herein, including plasmid vectors pSG5 and pND2, a plasmid containing a polynucleotide encoding secreted glutamic acid decarboxylase 55 (SGAD55) operably linked to a SV40 promoter (pSG5-sgad55), a plasmid containing a polynucleotide encoding a pro-apoptotic protein (hBAX) operably linked to an HCMV promoter (pND2-hBAX), and a plasmid containing a polynucleotide encoding SGAD55 and hBAX operably linked to an SV40 promoter (pSG5-sga55-bax).

As used in this disclosure, except where the context requires otherwise, the term "comprise" and variations of the term, such as "comprising," "comprises" and "comprised" are not intended to exclude other additives, components, integers or steps.

As used in this disclosure, the terms "graft" and "transplant" are used interchangeably and refer to an organ or tissue taken from the body and grafted into another area of the same individual or another individual.

As used in this disclosure, the term "allograft" comprises a graft of tissue between individuals of the same species but of disparate genotype; types of donors include cadaveric, living related, and living unrelated.

As used in this disclosure, the term "allogeneic" denotes individuals of the same species but of different genetic constitution.

As used in this disclosure, the term "allogeneic transplantation" denotes transplantation of an allograft.

As used in this disclosure, the term "DNA vaccine" comprises DNA sequences that code for immunogenic proteins located in appropriately constructed plasmids, which include strong promoters, which when injected into an animal are taken up by cells and the immunogenic proteins are expressed and elicit an immune response.

As used in this disclosure, the term "autoantigen" comprises an endogenous antigen that stimulates the production of autoantibodies, as in an autoimmune reaction, as well as part of such endogenous antigens, or modified endogenous antigens that elicit the same response as the full endogenous antigen, as will be understood by those with skill in the art with reference to this disclosure. For example, in the context of this disclosure secreted glutamic acid decarboxylase 55 and humanized BAX are both autoantigens.

As used in this disclosure, the term "donor antigen" comprises an antigen from an allograft that was transplanted into the recipient to take the place of defective or absent cells or tissues, such as for example skin grafts and islet cell transplants, and partial or whole organ transplants, including transplanted hearts, lungs, kidneys and livers, and that stimulates the production of antibodies that produce an immune reaction, as well as part of such donor antigens, or modified donor antigens that elicit the same response as the full donor antigen, as will be understood by those with skill in the art with reference to this disclosure. For example, in the context of this disclosure, secreted glutamic acid decarboxylase 55 is a donor antigen for skin grafts and islet cell transplants.

Examples of a pro-apoptotic protein include BAX (SEQ ID NO:2), a modified caspase, Tumor Necrosis Factor Receptor, Death Receptor 3 (DR3), Death Receptor 4 (DR4), Death Receptor 5 (DRS) and a FAS receptor. As used in this disclosure, the term "hBAX" and "BAX" are interchangeable.

As will be understood by those with skill in the art with reference to this disclosure, when reference is made to a protein encoded by a polynucleotide sequence, the protein includes "conservative substitutions" in which an amino acid is substituted for another amino acid that has similar properties, such that one skilled in the art of peptide chemistry would expect the secondary structure and hydropathic nature of the polypeptide to be substantially unchanged. A conservative substitution occurs when one amino acid residue is replaced with another that has a similar side chain. Amino acid residues having similar side chains are known in the art and include families with basic side chains (e.g., lysine (Lys/K), arginine (Arg/R), histidine (His/H)), acidic side chains (e.g., aspartic acid (Asp/Device 400), glutamic acid (Glu/E)), uncharged polar side chains (e.g., glycine (Gly/G), asparagine (Asn/N), glutamine (Gln/Q), serine (Ser/S), threonine (Thr/T), tyrosine (Tyr/Y), cysteine (Cys/C)), nonpolar side chains (e.g., alanine (Ala/A), valine (Val/V), leucine (Leu/L), isoleucine (Ile/I), praline (Pro/P), phenylalanine (Phe/F), methionine (Met/M), tryptophan (Trp/W)), branched side chains (e.g., threonine (Thr/T), valine (Val/V), isoleucine (Ile/I)) and aromatic side chains (e.g., tyrosine (Tyr/Y), phenylalanine (Phe/F), tryptophan (Trp/W), histidine (His/H)).

As used in this disclosure, a CpG motif is a polynucleotide region characterized by dinucleotides containing cytosine residues in the sequence CG. As will be understood by those with skill in the art with reference to this disclosure, bacterial DNAs containing unmethylated CpG motifs, stimulate the immune system in mammals to start a sequence of reactions leading to an immune reaction and inflammation. However, methylated CpG motifs may be applied to alleviate or inhibit the unwanted immune stimulation and inflammation by bacterial DNA.

Apoptotic cells are routinely processed by antigen presenting cells (APCs) like dendritic cells (DCs) to establish and maintain antigen-specific tolerance. DNA vaccines can induce apoptotic cells directly in vivo, and permit the engineering of the induced apoptotic cells. Unlike the use of immunosuppressants and co-stimulatory blockade, this is a "top down" approach that has the potential to induce specific immunoregulation via physiological modulation of APC function. In some embodiments, the present invention provides for the use of three different plasmid DNA constructs, and combinations thereof, as DNA vaccines to increase survival of allografts. Specific embodiments of each of the constructs causes increased survival of engrafted skin when injected into mice receiving skin allografts.

According to one embodiment of the present invention, there is provided a method of preventing, delaying the onset of, or treating the rejection of an allograft or an allogeneic transplant. In one embodiment, the method comprises, first, selecting a recipient in need of a graft or transplant and an allograft or allogeneic transplant donor. The selection can be made using standard methods as will be understood by those with skill in the art with reference to this disclosure.

According to one embodiment, the method further comprises engrafting tissue or transplanting a solid organ from the donor to the recipient to take the place of defective or absent cells or tissues. Engrafted tissues or transplanted organs can include a skin grafts, islet cell transplants, and partial or whole organ transplants including transplanted hearts, lungs, kidneys and livers.

According to one embodiment, the method further comprises administering to the recipient a DNA vaccine comprising one or more polynucleotides encoding (1) a pro-apoptotic protein, (2) an autoantigen or donor antigen, or (3) a pro-apoptotic protein and an autoantigen or donor antigen.

In one embodiment, a DNA vaccine for use in the present invention comprises a plasmid, the plasmid comprising a polynucleotide encoding a pro-apoptotic protein under the control of a promoter capable of expressing the polynucleotide encoding the pro-apoptotic protein.

In another embodiment, a DNA vaccine for use in the present invention comprises a plasmid, the plasmid comprising a polynucleotide encoding an autoantigen or a donor antigen operably linked to a promoter capable of controlling the expression of the polynucleotide encoding the autoantigen or the donor antigen, where the plasmid comprises a plurality of CpG motifs, and where at least some of the plurality of CpG motifs are methylated. In a preferred embodiment, the CpG motifs are methylated sufficiently to inhibit the recipient's immune response to unmethylated plasmid DNA. In a particularly preferred embodiment, the plasmid is resistant to digestion by the restriction endonuclease HpaII, which digests unmethylated but not methylated DNA. In another embodiment, the CpG motifs are methylated by SssI methylase.

In another embodiment, the plasmid comprising a polynucleotide encoding an autoantigen or a donor antigen can further comprise a polynucleotide encoding a pro-apoptotic protein under the control of a promoter capable of expressing the polynucleotide encoding the pro-apoptotic protein.

In a preferred embodiment, the promoter capable of expressing the polynucleotide encoding the autoantigen or the donor antigen, and the promoter capable of expressing the polynucleotide encoding the pro-apoptotic protein, are a single promoter.

In a preferred embodiment, the promoter capable of expressing the polynucleotide encoding the autoantigen or the donor antigen, or the promoter capable of expressing the polynucleotide encoding the pro-apoptotic protein, or both the promoter capable of expressing the polynucleotide encoding the autoantigen or the donor antigen, and the promoter capable of expressing the polynucleotide encoding the pro-apoptotic protein, maintain their promoter function after methylation.

In another embodiment, the plasmid comprises an internal ribosome entry site (IRES) sequence, to permit translation of the polynucleotide encoding the autoantigen or the donor antigen and the polynucleotide encoding the pro-apoptotic protein from the same transcript.

In another embodiment, the DNA vaccine of the present invention comprises a first plasmid and a second plasmid, or composition comprising a first plasmid and a second plasmid. The first plasmid comprises a polynucleotide encoding an autoantigen or a donor antigen under the control of a promoter capable of expressing the polynucleotide encoding the autoantigen or the donor antigen. The second plasmid comprises a polynucleotide encoding a pro-apoptotic protein under the control of a promoter capable of expressing the polynucleotide encoding the pro-apoptotic protein. The first plasmid comprises a plurality of CpG motifs, and at least some of the plurality of CpG motifs are methylated.

In a preferred embodiment, the promoter capable of expressing the polynucleotide encoding the autoantigen or the donor antigen maintains its promoter function after methylation. In another embodiment, the second plasmid comprises a plurality of CpG motifs, and at least some of the plurality of CpG motifs are methylated.

In a preferred embodiment, the promoter capable of expressing the polynucleotide encoding a pro-apoptotic protein maintains its promoter function after methylation.

In one embodiment, the DNA vaccine comprises the first plasmid and second plasmid in a ratio of between 1/1000 to 1000/1. In another embodiment, the composition comprises the first plasmid and second plasmid in a ratio of between 1/100 to 100/1. In another embodiment, the composition comprises the first plasmid and second plasmid in a ratio of between 1/10 to 10/1.

In one embodiment of the present invention, the recipient is a mammal. In another embodiment, the recipient is a human.

In another embodiment, the autoantigen is selected from the group consisting of carbonic anhydrase II, collagen, CYP2D6 (cytochrome P450, family 2, subfamily Device 400, polypeptide 6), glutamic acid decarboxylase, secreted glutamic acid decarboxylase 55, SEQ ID NO:1, insulin, myelin basic protein and SOX-10 (SRY-box containing gene 10).

In another embodiment, the pro-apoptotic protein is selected from the group consisting of BAX, SEQ ID NO:2, a modified caspase, Tumor Necrosis Factor Receptor, Death Receptor 3 (DR3), Death Receptor 4 (DR4), Death Receptor 5 (DR5) and a FAS receptor.

In a preferred embodiment, the internal ribosome entry site sequence is an internal ribosome binding site from the EMC virus, SEQ ID NO:3.

The method comprises administering to the recipient one or more than one dose of a DNA vaccine according to the present invention. In a preferred embodiment, the DNA vaccine is administered in a plurality of doses. In another preferred embodiment, the dose is between about 0.001 mg/Kg of body weight of the recipient and about 100 mg/Kg of body weight of the recipient. In another preferred embodiment, the dose is between about 0.01 mg/Kg of body weight of the recipient and about 10 mg/Kg of body weight of the recipient. In another preferred embodiment, the dose is between about 0.1 mg/Kg of body weight of the recipient and about 1 mg/Kg of body weight of the recipient. In another preferred embodiment, the dose is about 0.05 mg/Kg of body weight of the recipient. In a preferred embodiment, the recipient is a human and the dose is between about 0.5 mg and 5 mg. In another preferred embodiment, the recipient is a human and the dose is between about 1 mg and 4 mg. In another preferred embodiment, the recipient is a human and the dose is between about 2.5 mg and 3 mg. In another preferred embodiment, the dose is administered weekly between 2 times and about 100 times. In another preferred embodiment, the dose is administered weekly between 2 times and about 20 times. In another preferred embodiment, the dose is administered weekly between 2 times and about 10 times. In another preferred embodiment, the dose is administered weekly 4 times. In another preferred embodiment, the dose is administered only once.

Administering the one or more than one dose of a DNA vaccine to the recipient can be accomplished by any suitable route, as will be understood by those with skill in the art with reference to this disclosure. In one embodiment, administering to the recipient one or more than one dose of a substance or a composition is performed by a route selected from the group consisting of epidermal, intradermal, intramuscular, intranasal, intravenous and oral. In a preferred embodiment the DNA vaccine is administered proximal to the site of the allograft or allogeneic transplant. For example, the plasmid DNA does not have to be injected into a skin graft, but can be injected directly intradermally into the recipient.

When the method comprises administering a first plasmid and a second plasmid, the first plasmid and the second plasmid can be administered either sequentially or simultaneously, as will be understood by those with skill in the art with reference to this disclosure.

When the method comprises administering a first plasmid and a second plasmid, the method can further comprise inducing a donor-specific immune response that elevates Th2-like activity, which can include inducing expression of Il-4 in the allograft.

When the method comprises administering a first plasmid and a second plasmid, the method can further comprise inducing expression of FcαIIb in the allograft.

When the method comprises administering a first plasmid and a second plasmid, the method can further comprise decreasing expression of pro-inflammatory Tnf-α and Ifn-γ genes.

In one embodiment, the method further comprises administering a dose of one or more than one immunosuppressant agent before, on the day of, and/or after engraftment or transplantation.

When the method comprises administering one or more than one immunosuppressant agent, the one or more than one immunosuppressant agent can be administered simultaneously, separately or sequentially.

In one embodiment, the one or more than one immunosuppressant agent is selected from the group consisting of corticosteroids, glucocorticoids. cyclophosphamide, 6-mercaptopurine (6-MP), azathioprine (AZA), methotrexate cyclosporine, mycophenolate mofetil (MMF), mycophenolic acid (MPA), tacrolimus (FK506), sirolimus ([SRL] rapamycin), everolimus (Certican), mizoribine, leflunomide, deoxyspergualin, brequinar, azodicarbonamide, vitamin D analogs, such as MC1288 and bisindolylmaleimide VIII, antilymphocyte globulin, antithymocyte globulin (ATG), anti-CD3 monoclonal antibodies, (Muromonab-CD3, Orthoclone OKT3), anti-interleukin (IL)-2 receptor (anti-CD25) antibodies, (Daclizumab, Zenapax, basiliximab, Simulect), anti-CD52 antibodies, (Alemtuzumab, Campath-1H), anti-CD20 antibodies (Rituximab, Rituxan), anti-tumor necrosis factor (TNF) reagents (Infliximab, Remicade, Adalimumab, Humira) and LFA-1 inhibitors (Efalizumab, Raptiva).

The dosages of the immunosuppressant agents will vary depending on the individual to be treated, the route of administration, and the nature and severity of the condition to be treated. For example, an initial dose of about 2 to 3 times the maintenance dose may suitably be administered about 4 to 12 hours before transplantation, followed by a daily dosage of 2 to 3 times the maintenance dose for one to two weeks, before gradually tapering down at a rate of about 5% a week to reach the maintenance dose.

The skilled person may determine those dosages that provide a therapeutic amount of an immunosuppressant agent at a level that is tolerated. In a preferred embodiment, the method further comprises administering a single dose of antilymphocyte globulin of about 1.6 mg/20 g of body weight on the day of engraftment or transplantation. In another preferred embodiment, rapamycin may be applied at a dosage range of from about 0.05 to about 15 mg/kg/day, more preferably from about 0.25 to about 5 mg/kg/day and most preferably from about 0.5 to about 1.5 mg/kg/day. Ideally, the administration of doses of one or more than one immunosuppressant agent can be curtailed after effective treatment with the DNA vaccine.

In one embodiment, the method further comprises, after administering the DNA vaccine, monitoring the recipient for rejection of the allograft of transplant. In a preferred embodiment, the recipient is monitored for rejection of the allograft or transplant after tapering off or discontinuing the administration of immunosuppressant agents.

Example 1

Plasmid DNA Constructs, Methylation, and Amplification

The following examples were designed to test whether our pro-apoptotic DNA vaccination strategy is applicable to prevention of solid allograft rejection. Our model suggests that injection of plasmid DNA coding for BAX near the allograft would cause recruitment of APCs after induction of apoptotic cells, the APCs would process donor antigens under tolerogenic conditions, and a protective, immunoregulatory response would be induced.

In order to compare the efficacy of different DNA vaccines for preventing, delaying the onset of or treating the rejection of an allograft or organ transplant according to the present invention, several plasmids were prepared. Referring now to FIG. 1, there are shown, respectively, a schematic depiction of pSG5, pND2, pSG5-SGAD55, and pND2-hBAX.

Plasmid pSG5 was purchased from Stratagene (San Diego, Calif. US). The remaining plasmids were produced using standard techniques. Plasmid pND2-BAX carries a BAX cDNA under transcriptional control of the CMV promoter, and plasmid pSG5-SGAD55 carries a cDNA construct encoding a secreted form of GAD65 under transcriptional control of the SV-40 promoter.

With reference to FIG. 1, the abbreviations shown are standard, as will be understood by those with skill in the art with reference to this disclosure, including: AMP (ampicillin resistance gene for selection in $E.\ coli$); BGH pA (bovine growth hormone polyadenylation sequence); ColE1 origin (origin of replication in $E.\ coli$); f1 origin (origin of replication for filamentous phage f1 to generate single stranded DNA); hBAX (human bax cDNA), SEQ ID NO: 2; HCMV promoter (promoter from cytomegalovirus); HCMV intron (intron from cytomegalovirus); MCS (multiple cloning site); pUC origin (origin of replication for $E.\ coli$ from pUC plasmid); sgad55 (secreted GAD cDNA construct), SEQ ID NO:1; SV40 promoter (simian virus 40 promoter); SV40 pA (simian virus 40 polyadenylation sequence); and T7 (T7 promoter).

Plasmids pSG5 and pSG-SGAD55 were methylated to produce methylated pSG5, and methylated pSG5-SGAD55, by amplification in $E.\ coli$ strain ER1821 carrying a plasmid encoding the SssI methylase (New England Biolabs, Beverly, Mass. US). SssI methylates the dinucleotide motif CpG in DNA in a manner corresponding to mammalian methylases by covalently adding a single methyl group to the dinucleotide motif CpG.

Plasmid DNA was isolated after amplification in $Escherichia\ coli$ strain DH5a or ER1821 using the Endofree Plasmid DNA Purification Kit (Qiagen, Valencia, Calif.). Successful methylation was confirmed by digesting the isolated plasmid DNA with the restriction enzyme HpaII which digests unmethylated but not methylated DNA, where resistance to HpaII digestion indicates successful methylation.

Example 2

Skin Allograft Survival

An allograft skin transplant model was used as proof of principle because it is one of the most difficult models for prevention of organ rejection. A combination of two of the plasmid constructs (2-plasmid vaccine coding for secreted GAD, i.e., SGAD55, and pro-apoptotic BAX, with one plasmid methylated with SssI methylase) has been used successfully as a DNA vaccine for therapy of type 1 diabetes in NOD mice. However, each of the two DNA constructs (plasmid DNA coding for BAX alone, or SssI-methylated plasmid DNA coding for SGAD55 alone) were found to be ineffective for therapy of diabetes on their own. Unexpectedly, we now find that all three alternatives can prevent skin allograft rejection.

The effects of i.d. injection of different DNA vaccines were investigated m C57BL/6 mice receiving minimum immunosuppression and skin allografts from BALB/c mice. 0.7×0.7 cm full-thickness back skin grafts from BALB/c donors or C3H third party were transplanted onto the back of C57BL/6 recipients. With the exception of the untreated group, anti-lymphocyte immunoglobulin ALG (1.6 mg/20 g BW) was given i.p. once on day 0. Fifty μg of the following plasmid DNAs: 1) vector alone, 2) DNA coding for BAX alone, 3) SssI-methylated DNA coding for SGAD55 alone (Msgad55), or 4) DNA coding for BAX together with SssI-methylated DNA coding for SGAD55 (Msgad55+bax), were injected i.d. near the skin graft on day 0, 3, 7, and then weekly. Rapamycin (1 mg/kg) was injected i.p. daily from days 0-27. Bandages were removed on day 10, and skin graft rejection was defined as 85% loss of the graft area, and confirmed by pathological analysis.

Figure 2A:
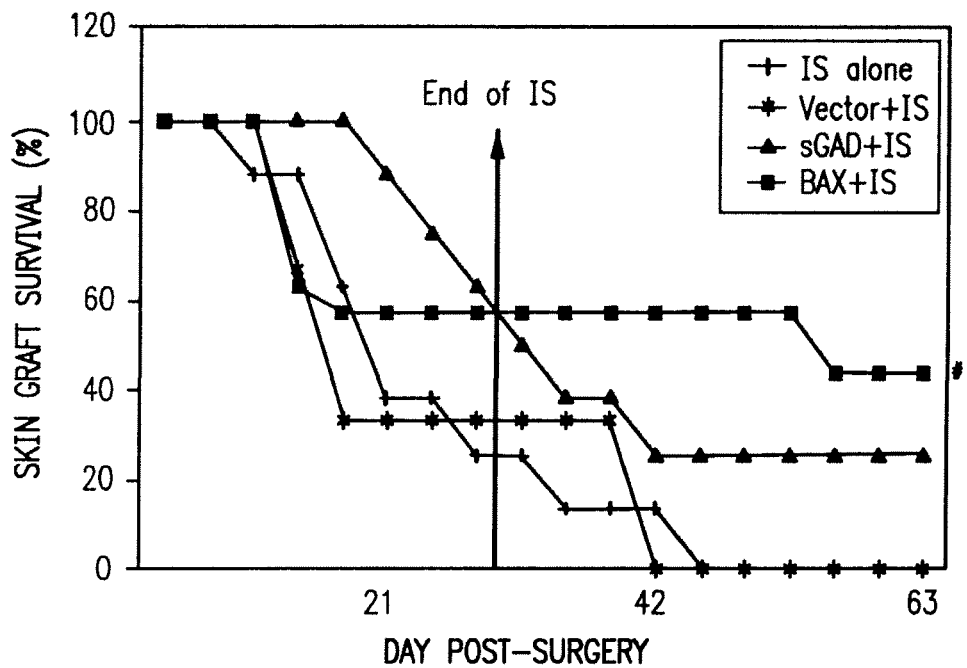
FIGS. 2A-2B show the effects of DNA vaccination on skin allograft survival. 7-week-old, age matched C57BL/6 recipients (N=8-14) received skin grafts from BALB/c donor under minimum immune suppression regimen (IS) that was ended on day 28, and received a weekly i.d. injection of 50 μg of the indicated vaccine. The BAX and sGAD vaccines are non-CpG-methylated plasmid DNA coding for BAX and sGAD alone, respectively. The MsGAD DNA vaccine consists of CpG-methylated plasmid DNA coding for sGAD alone. The MsGAD-BAX vaccine consists of a 4:1 ratio of MsGAD:BAX plasmid DNA.

FIG. 2A shows that non-methylated plasmid DNA coding for BAX alone could significantly delay skin rejection compared to mice receiving vector DNA alone, but that non-methylated plasmid DNA coding for sGAD alone did not. Injection of non-methylated plasmid vector alone had no significant effect on allograft survival compared to non-vaccinated, immunosuppressed mice.

Figure 2B:
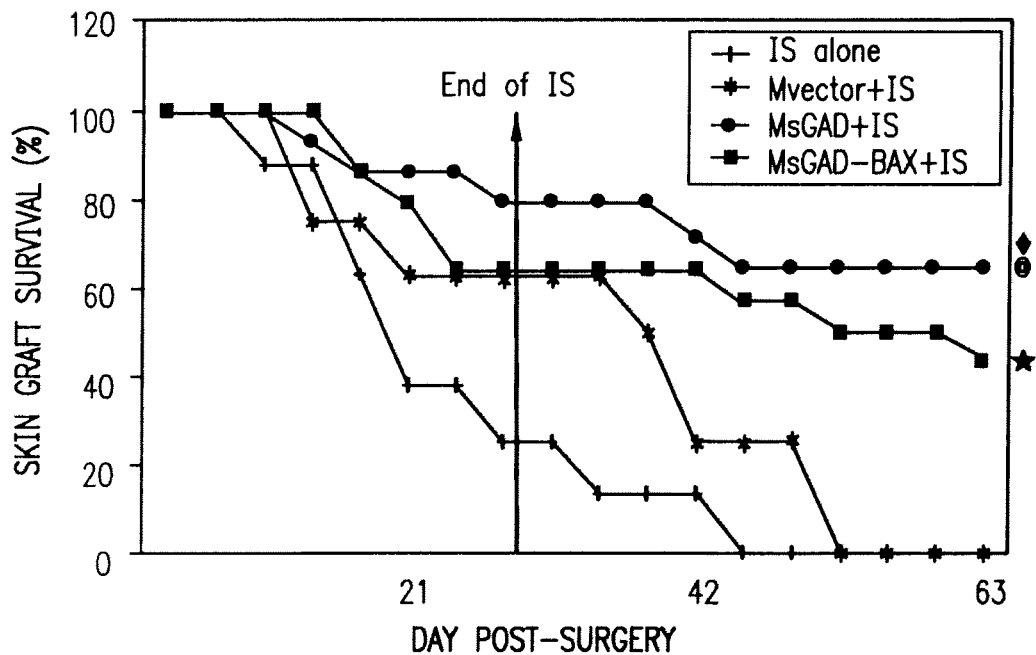

In addition, we investigated the effects of CpG-methylation of vaccine DNA and of combined delivery of plasmid DNA coding for sGAD and BAX on skin allograft survival. CpG-methylation of the vaccine coding for sGAD alone (MsGAD) resulted in increased allograft survival (FIG. 2B), which was significant compared to mice immunized with the non-methylated vaccine coding for sGAD alone and CpG-methylated vector control. However, combined delivery of CpG-methylated plasmid DNA coding for secreted GAD and plasmid DNA coding for BAX resulted in increased survival only when compared with mice vaccinated with vector controls and non-immunized mice, which indicated an antagonistic effect of BAX.

Without being held to any particular underlying mechanisms behind the observed effects, we suspect that it may involve donor antigen-specific immunoregulation for the constructs coding for BAX, based on our previous model for a pro-apoptotic DNA vaccination strategy. We do not know what the mechanism of action is for the third construct (SssI-methylayed DNA coding for SGAD55).

Example 3

RNA Isolation and qPCR

We investigated the effects of the MsGAD-BAX vaccine, which showed efficacy in both prevention of skin allograft rejection and amelioration of new-onset diabetes in NOD mice in previous work, and of the BAX vaccine on the expression of chosen genes m transplanted BALB/c skin and freshly isolated LNs of recipient C57BL/6 mice.

For immune analysis, draining lymph nodes of mice receiving ALG and rapamycin alone, and from mice treated with the vaccine coding for BAX and SGAD55, were taken 2 weeks after transplantation. Lymph nodes were cultured in the presence of inactivated splenocytes from C57/BL6 (recipient), BALB/c (donor), or DBA (third party) as sources of antigens, and CD4+CD25+ and CD4+CD25− cells were isolated for proliferation assays.

Quantitative PCR analysis of expression of selected genes was performed with skin allografts, cultured lymph nodes, and CD4+CD25+/CD25− cells isolated from proliferation assays. In addition to the Il-4, Il-10, Tgf-β1, Tnf-α, and Ifn-γ genes, we quantified the expression of genes coding for the co-stimulatory molecules CD80 and CD86 found on APCs, the transcriptional factor FOXP3 synthesized by regulatory T cells (Tregs), and the inhibitory receptor FcγRIIB and IL-1-antagonist IL-1RA cytokine, which are both up-regulated in murine tolerogenic DCs.

Total RNA was isolated using Trizol LS reagent (Invitrogen, Cartsbad, Calif.) from freshly taken skin allograft and draining LNs 2 weeks after transplantation. RNA was also isolated from LNs cultured for 3 days in as described above. qPCR was performed using the iCycler system and SYBR green (Bio Rad, Hercules, Calif.) with 200 ng of total RNA as template and primers specific for the chosen cDNAs, and for the GAPDH cDNA as a housekeeping gene.

Figure 3A:
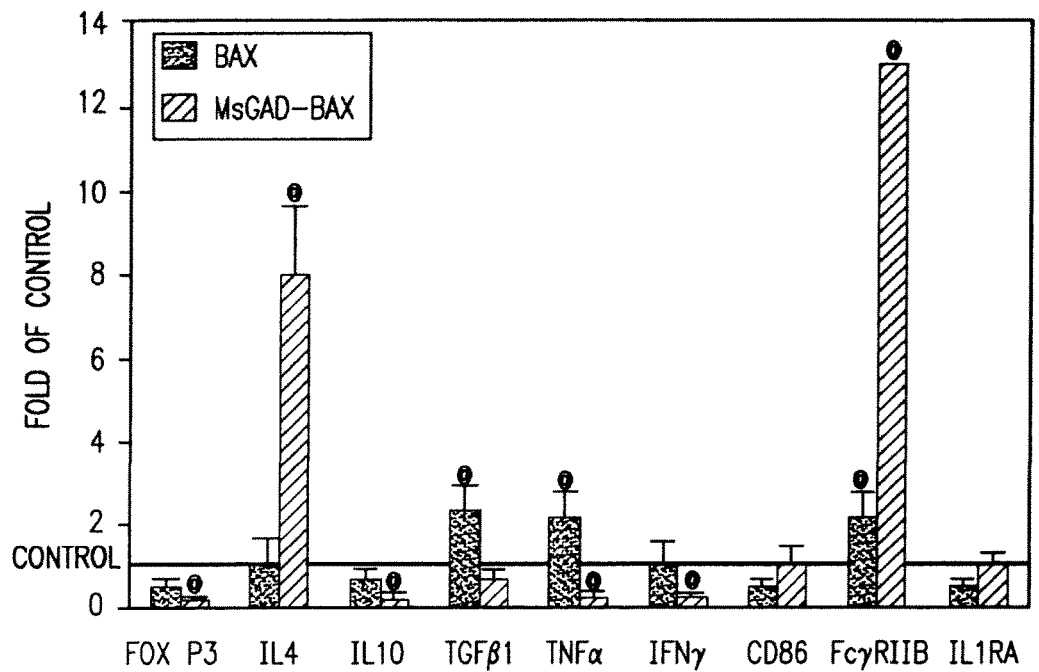
FIGS. 3A-3C shows the results of quantitative gene expression analysis in skin and LNs of recipient mice. C57BL/6 mice under minimum immunosuppression received BALB/c skin grafts and were immunized with the BAX or MsGAD-BAX DNA vaccine. Fresh skin allografts (3A) and fresh lymph nodes (LNs) (3B) were taken 2 weeks after transplant for qPCR analysis. In addition, LNs were stimulated with self, donor, or third-party (C3H) antigens for analysis (3C). Results are shown as fold of gene expression relative to non-vaccinated C57BL/6 mice under minimum immunosuppression (control).
Figure 3B:
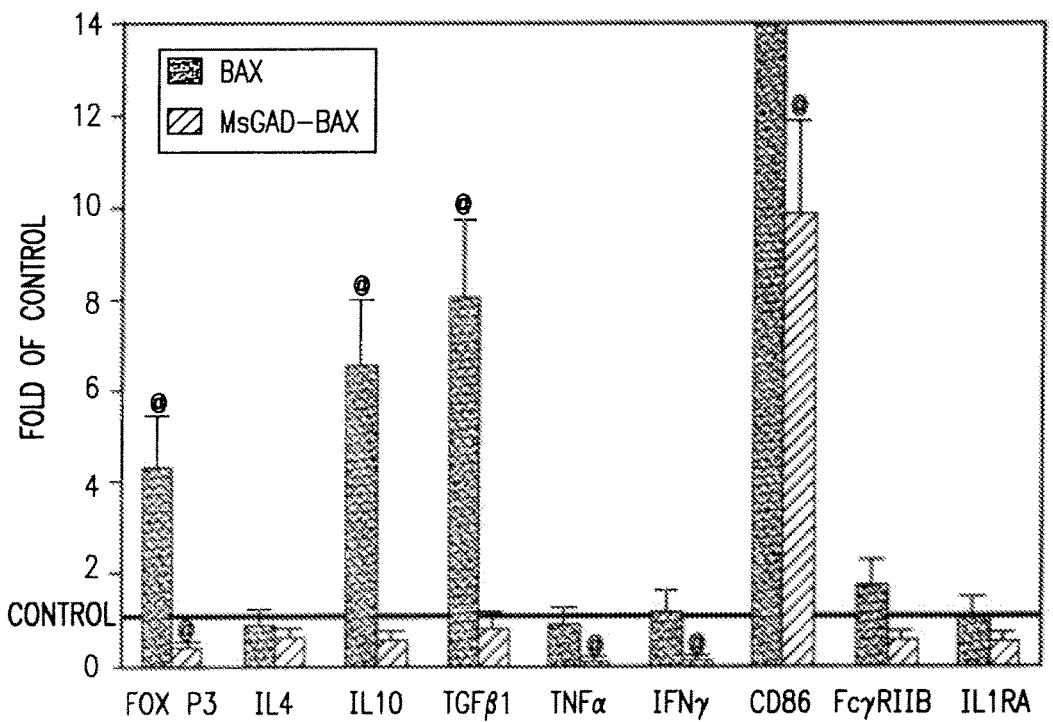

In the transplanted skin, the most striking differences between the two vaccines were increased expression of the Il-4 and FcγrIIb genes and decreased expression of the Tnf-α and Ifn-γ genes in mice immunized with MsGAD-BAX (FIG. 3A). In LNs, the most apparent differences were increased expression of the Foxp3, Il-10, Tgf-β1, and Cd86 genes in mice immunized with BAX, and decreased expression of the Tnf-α and Ifn-γ genes in mice immunized with MsGAD-BAX (FIG. 3B). Increased expression of Cd86 was also observed in mice immunized with MsGAD-BAX, but to an extent that was proportional to the amount of delivered Bax cDNA. No significant change in the expression of the Cd80 gene was observed (data not shown). These data indicated that the two vaccines induced clearly distinct immune responses.

Figure 3C:
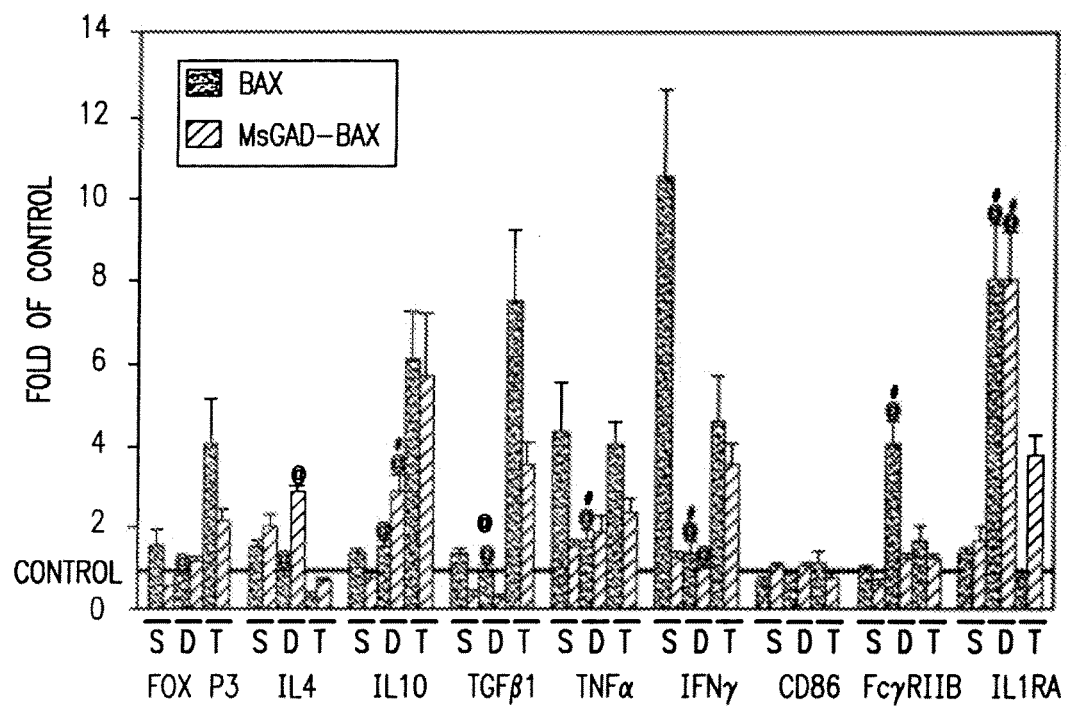

Several pieces of evidence indicated that BAX and MsGAD-BAX induced donor-specific immune responses. First, gene expression analysis of LNs from C57BL/6 mice receiving BALB/c skin allografts and cultured for 3 days revealed several significant differences when cells were stimulated with self, donor, or third party antigens (FIG. 3C). Compared to stimulation with third party antigens, cells from mice immunized with BAX and MsGAD-BAX and stimulated with donor antigens showed a significant change in expression in 8 and 5 of the 9 chosen genes, respectively. In contrast, compared to stimulation with self antigens, cells from mice immunized with BAX and MsGAD-BAX and stimulated with donor antigens showed change in expression in 4 and 2 of the 9 genes, respectively. These results indicated that the gene expression profile after donor antigen stimulation was markedly different from the third party antigen profile and more similar to the self antigen profile. In addition, the finding that genes like FcγrIIb and Il-1ra, which are up-regulated in tolerogenic DCs, were induced only when stimulated with donor antigens corroborated the notion of a donor-specific tolerogenic response.

Example 4

Adoptive Cell Transfer

Cells from spleen and draining axillary and cervical lymph nodes (LNs) were isolated 2 weeks post donor skin graft transplant and suspended in PBS; $5\times10^6$ total cells per recipient were injected i.p. at day −2, and 3 Gy TBI irradiation was given on day −3. Donor or third party back skin grafts were transplanted on day 0, and rapamycin (1 mg/kg) was given i.p. daily.

Figure 4:
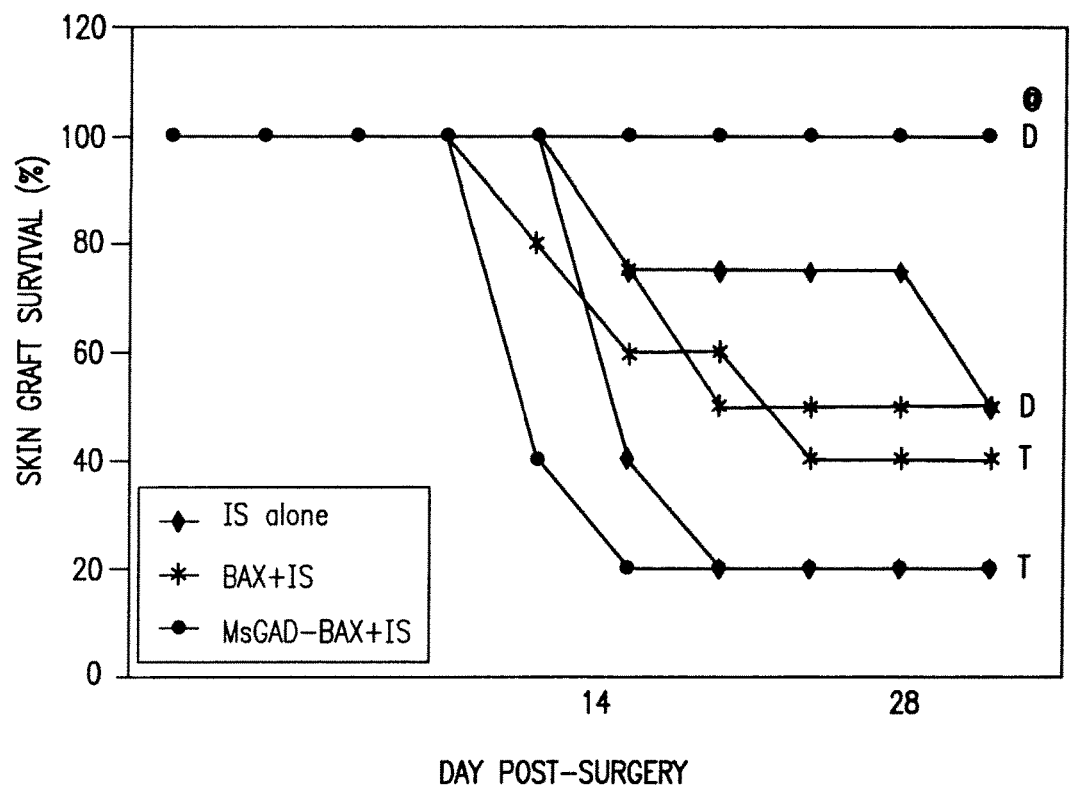
FIG. 4 shows the results of the adoptive transfer of immune cells from pooled LNs and spleen. Adoptive transfer donor (C57BL/6) received BALB/c skin graft and minimum immunosuppression. Splenocytes and draining lymph node cells were then isolated on day 14, and injected i.p. on day −2 into adoptive transfer recipients (C57BL/6, N=4-5) receiving donor (BALB/c, D) or third party (C3H, T) skin grafts at day 0. The recipients also received 3 Gy irradiation at day −3, and daily rapamycin i.p. @, P<0.05 compared to third party.

Results from adoptive transfer experiments indicated and LN cells from C57BL/6 mice receiving BALB/c skin graft and immunized with MsGAD-BAX could transfer survival of donor but not third party graft (FIG. 4). In contrast, cells from mice immunized with BAX did not significantly prevent rejection of either donor or third party graft.

Example 5

MLR

Figure 5:
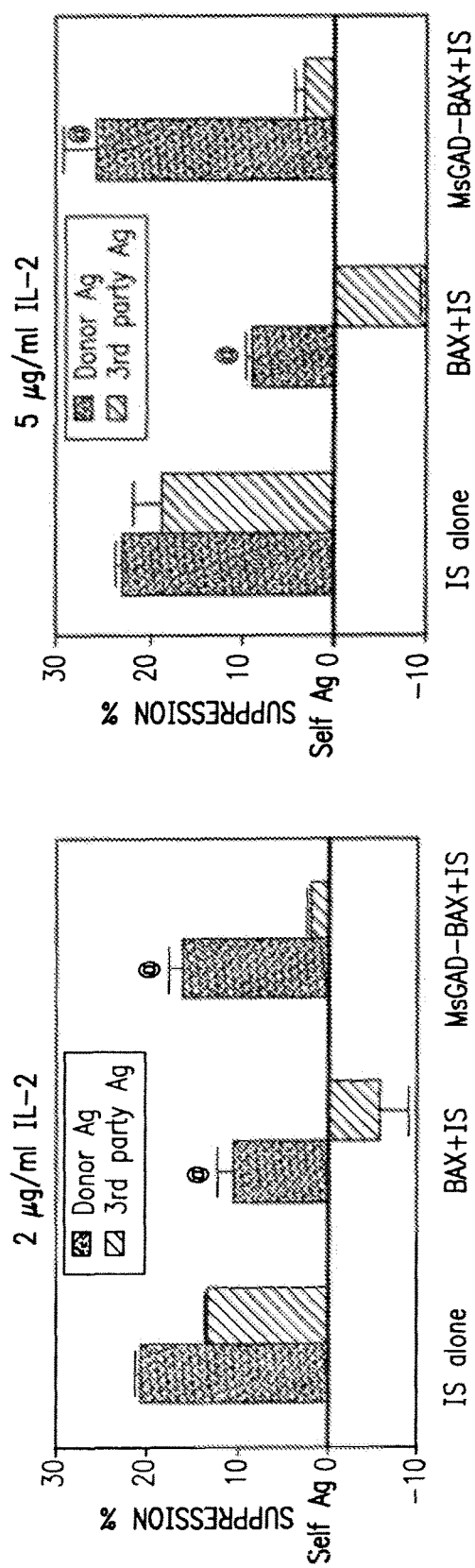
FIG. 5 shows the results of mixed lymphocyte reactions where LN cells were isolated from recipients receiving donor skin grafts and immune regimen for 2 weeks, and $4 \times 10^5$ LN cells were mixed with $4 \times 10^5$ mitomycin treated splenocytes from BALB/c donor or C3H third-party mice in presence of 2 or 5 μg/ml IL-2. @, P<0.05 compared to third party antigens.

LNs were dispersed and stimulated with mitomycin C-treated splenocytes from C57BL/6, BALB/c, and C3H mice for 5 days with 2 or 5 μg/ml IL-2 for MLR using 2 μM CFSE-labeled LN cells. Results from MLR using CSFE-labeled LN cells cultured with inactivated splenocytes from donor and third party antigens also indicated a donor-specific immune response for each vaccine. In the presence of 2 µg/ml IL-2, LN cells from non-vaccinated, immunosuppressed mice did not show a significant difference in suppression when stimulated with donor or third party antigens (FIG. 5A). In contrast, LN cells from mice immunized with BAX or MsGAD-BAX showed a significant difference in their response to third party antigen compared to donor antigen. Culture with 5 µg/ml IL-2 did not restore proliferation and accentuated these differences (FIG. 5B).

CONCLUSION

Specific embodiments of the present invention described herein address the problems of preventing rejection of allografts without having to know the identity of the donor antigens, and of reducing the need for immunosuppressants that are known to have serious side-effects over the long term. Our results indicate that "pro-apoptotic" DNA vaccination can be applied successfully to solid organ transplantation. Injection of BAX DNA appears to induce a donor-specific immunoregulatory response that contributes to increased graft survival.

One explanation for the observed effects is that vaccination with plasmid DNA coding for BAX induces apoptotic cells that recruit antigen presenting cells. The antigen presenting cells process the tolerogenic apoptotic cells together with donor antigens and protects the allograft, most likely via multiple immune mechanisms. However, considering that expression of Foxp3, Il-10 and Tgf-β1 was consistently higher in non-vaccinated, immunosuppressed animals, other mechanisms of tolerance induced by our DNA vaccination strategy are likely to play a role in expressing graft survival. Unexpectedly, injection of SssI-methylated coding for SGAD55 alone could prolong graft survival. The same vaccine was ineffective for treatment of type diabetes in our previous studies. Consequently, the underlying mechanism for graft survival using this approach remains to be determined.

Our data indicates that both the BAX and MsGAD-BAX vaccines induced a donor-specific immune response, albeit via two different mechanisms. The BAX vaccine caused changes in gene expression mainly in fresh LNs, most likely because of the recruitment of APCs to LNs after plasmid DNA-mediated induction of apoptosis. Increased expression of Cd86 associated with delivery of the bax cDNA was not linked with concomitant Cd80 expression, which indicated induction of Cd86. The CD86 molecule is the main ligand for CD28 and promotes inflammation. Significantly, LN cells of BAX-immunized mice showed highly increased expression of the Tnf-α and lfn-γ genes when stimulated with self antigens, which was not observed with cells stimulated with donor antigens or with cells from mice immunized with MsGAD-BAX and stimulated with self antigens. These results suggest that induction of recipient apoptotic cells near the allograft could have amplified the autoimmune response that is known to be induced by a skin allograft via an indirect alloresponse.

In addition, fresh LNs and LN cells from BAX-immunized mice stimulated with third party antigen showed increased expression of Foxp3, Il-10, and Tgf-βI, which is associated with CD4+CD25+ regulatory T cell activity. However, it is unlikely that such cells were responsible alone for increased allograft survival, because adoptive transfer of spleen and LN cells from BAX-immunized mice did not prevent rejection of either donor or third party allografts. Rather, these results suggested that the BAX vaccine promoted graft survival via a different mechanism, like clonal deletion. The lesser efficacy of the BAX vaccine could have been the result of the autoimmune response it induced. Nevertheless, it the efficacy of the vaccine may be improved using CpG-methylation of plasmid DNA to lower inflammation resulting from interaction between bacterial plasmid DNA and TLR-9, and by injecting the DNA outside of the inflammatory milieu induced by the allograft.

In contrast with BAX, the MsGAD-BAX vaccine induced expression in the allograft of Il-4, which indicated Th2-like activity, and of FcγIIb, which is up-regulated in tolerogenic DCs. Moreover, the MsGAD-BAX vaccine caused decreased expression of the pro-inflammatory Tnf-α and Ifn-γ genes in both transplanted skin and fresh LNs, did not appear to promote autoimmunity, and induced cells that transferred graft survival in a donor-specific manner. Notably, GAD is found in skin, which we confirmed in skin allografts using qPCR (data not shown), and is up-regulated in inflamed tissues. Therefore, the sGAD polypeptide may act as a regulatory autoantigen that prevents allograft rejection. Indeed, the strongest evidence that autoimmunity plays a role in allograft rejection comes from experiments where administration of autoantigens present in the donor graft can prevent rejection of lung or heart allografts, or accelerate rejection when injected with Freund's adjuvant into recipient. Our finding that Il-4 expression was increased in skin allograft corroborates the notion that this cytokine can be a key element in the process.

In conclusion, plasmid DNA-mediated induction of recipient apoptotic cells and delivery of an allograft-associated autoantigen form the basis of a new DNA vaccination strategy that targets allograft-induced autoimmunity to prevent transplant rejection. This approach, which is readily amenable to manipulation at the molecular and cellular levels for further improvement, provides a promising means to control chronic rejection in which allograft-induced autoimmunity is thought to play a significant role.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to U.S. patent application Ser. No. 13/543,567, are incorporated herein by reference in their entirety. Aspects of the embodiments can be modified, if necessary, to employ concepts of the various patents, applications and publications to provide further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for inducing a tolerogenic response, comprising intradermally administering to a graft or transplant recipient an effective amount of a DNA vaccine composition, thereby inducing a tolerogenic response to prevent or minimize (i) late-onset chronic graft or transplant rejection, and/or (ii) transplant induced autoimmunity,
   wherein the DNA vaccine composition comprises (a) a first plasmid comprising a polynucleotide encoding a pro-apoptotic protein operably linked to a promoter that controls the expression of the polynucleotide encoding the pro-apoptotic protein, wherein the encoded pro-apoptotic protein is selected from the group consisting of BAX (SEQ ID NO.:2), Death Receptor 3 (DR3), Death Receptor 4 (DR4), Death Receptor 5 (DR5), and a FAS receptor; and (b) a second plasmid comprising a polynucleotide encoding an autoantigen or a donor antigen operably linked to a promoter that controls the expression of the polynucleotide encoding the autoantigen or donor antigen, and comprising a plurality of CpG motifs, wherein at least some of the plurality of CpG motifs are methylated and resistant to digestion by restriction endonuclease HpaII.

2. The method of claim 1, wherein the graft or transplant comprise tissues or organs selected from the group consisting of skin grafts, islet cell transplants, and partial or whole organ transplants.

3. The method of claim 2, wherein the partial or whole organ transplants are selected from the group consisting of hearts, lungs, kidneys and livers.

4. The method of claim 1, wherein the first and/or second plasmid is methylated with an SssI DNA methyltransferase.

5. The method of claim 1, wherein the first plasmid and second plasmid contain the same promoter.

6. The method of claim 1, wherein the DNA vaccine comprises the first plasmid and the second plasmid in a ratio of between 1/10 to 10/1.

7. The method of claim 1, wherein the autoantigen or donor antigen is selected from the group consisting of carbonic anhydrase II, collagen, CYP2D6 (cytochrome P450, family 2, subfamily Device 400, polypeptide 6), glutamic acid decarboxylase, secreted glutamic acid decarboxylase 55 (SEQ ID NO:1), insulin, myelin basic protein and SOX-10 (SRY-box containing gene 10).

8. The method of claim 1, wherein the DNA vaccine prevents or minimizes late-onset chronic allograft or allogeneic transplant rejection.

9. The method of claim 1, wherein the DNA vaccine is administered in a plurality of doses.

10. The method of claim 1, wherein the DNA vaccine is administered weekly between two times and 100 times.

11. The method of claim 1, wherein the DNA vaccine is administered proximal to the graft or transplant site.

12. The method of claim 1, further comprising administering an immunosuppressant agent before, on the day of, and/or after engraftment or transplantation.

13. The method of claim 12, wherein the immunosuppressant agent is administered simultaneously, separately or sequentially with the DNA vaccine.

14. The method of claim 12, wherein the immunosuppressant agent is selected from the group consisting of corticosteroids, glucocorticoids, cyclophosphamide, 6-mercaptopurine, azathioprine, methotrexate cyclosporine, mycophenolate mofetil, mycophenolic acid, tacrolimus, sirolimus, everolimus, mizoribine, leflunomide, deoxyspergualin, brequinar, azodicarbonamide, vitamin D analogs, antilymphocyte globulin, antithymocyte globulin, anti-CD3 monoclonal antibodies, anti-interleukin-2 receptor (anti-CD25) antibodies, anti-CD52 antibodies, anti-CD20 antibodies, anti-tumor necrosis factor reagents and LFA-1 inhibitors.

15. The method of claim 12, comprising administering a single dose of anti-lymphocyte globulin, at a dose ranging from about 1.6 mg/20 g of body weight, on the day of engraftment or transplantation.

16. The method of claim 12, comprising administering rapamycin at a dose ranging from 0.05 mg/day to 15 mg/day.

* * * * *

SEQUENCE LISTING

<160> NUMBER OF SEQ ID NOS: 3

<210> SEQ ID NO 1
<211> LENGTH: 1638
<212> TYPE: DNA
<213> ORGANISM: Homo sapiens

<400> SEQUENCE: 1

| | | | | | |
|---|---|---|---|---|---|
| atgtacagga | tgcaactcct | gtcttgcatt | gcactaagtc | ttgcacttgt | cacaaacagt | 60 |
| gcacctactt | acgcgtttct | ccatgcaaca | gacctgctgc | cggcgtgtga | tggagaaagg | 120 |
| cccactttgg | cgtttctgca | agatgttatg | aacattttac | ttcagtatgt | ggtgaaaagt | 180 |
| ttcgatagat | caaccaaagt | gattgatttc | cattatccta | atgagcttct | ccaagaatat | 240 |
| aattgggaat | tggcagacca | accacaaaat | ttggaggaaa | ttttgatgca | ttgccaaaca | 300 |
| actctaaaat | atgcaattaa | acagggcat | cctagatact | tcaatcaact | ttctactggt | 360 |
| ttggatatgg | ttggattagc | agcagactgg | ctgcatcaa | cagcaaatac | taacatgttc | 420 |
| acctatgaaa | ttgctccagt | atttgtgctt | ttggaatatg | tcacactaaa | gaaaatgaga | 480 |
| gaaatcattg | gctggccagg | gggctctggc | gatgggatat | tttctcccgg | tggcgccata | 540 |
| tctaacatgt | atgccatgat | gatcgcacgc | tttaagatgt | tcccagaagt | caaggagaaa | 600 |
| ggaatggctg | ctcttcccag | gctcattgcc | ttcacgtctg | aacatagtca | tttttctctc | 660 |
| aagaagggag | ctgcagcctt | agggattgga | agagacagcg | tgattctgat | taaatgtgat | 720 |
| gagagaggga | aaatgattcc | atctgatctt | gaaagaagga | ttcttgaagc | caaacagaaa | 780 |
| gggtttgttc | ctttcctcgt | gagtgccaca | gctggaacca | ccgtgtacgg | agcatttgac | 840 |
| cccctcttag | ctgtcgctga | catttgcaaa | aagtataaga | tctggatgca | tgtggatgca | 900 |
| gcttggggtg | ggggattact | gatgtcccga | aaacacaagt | ggaaactgag | tggcgtggag | 960 |
| agggccaact | ctgtgacgtg | gaatccacac | aagatgatgg | gagtcccttt | gcagtggtct | 1020 |
| gctctcctgg | ttagagaaga | gggattgatg | cagaattgca | accaaatgca | tgcctcctac | 1080 |
| ctctttcagc | aagataaaca | ttatgacctg | tcctatgaca | ctggagacaa | ggccttacag | 1140 |
| tgcggacgcc | acgttgatgt | ttttaaacta | tggctgatgt | ggagggcaaa | ggggactacc | 1200 |
| gggtttgaag | cgcatgttga | taatgtgttg | gagttggcag | agtatttata | caacatcata | 1260 |
| aaaaaccgag | aaggatatga | gatggtgttt | gatgggaagc | ctgaggacac | aaatgtctgc | 1320 |
| ttctggtaca | ttcctccaag | cttgcgtact | ctggaagaca | atgaagagag | aatgagtcgc | 1380 |
| ctctcgaagg | tggctccagt | gattaaagcc | agaatgatgg | agtatggaac | cacaatggtc | 1440 |
| agctaccaac | ccttgggaga | caaggtcaat | ttcttccgca | tggtcatctc | aaacccagcg | 1500 |
| gcaactcacc | aagacattga | cttcctgatt | gaagaaatag | aacgccttgg | acaagattta | 1560 |
| taataacctt | gctcaccaag | ctgttccact | tctctaggta | gcgacctcga | gcggccgctc | 1620 |
| gagggggggc | ccggtacc | | | | | 1638 |

<210> SEQ ID NO 2
<211> LENGTH: 579
<212> TYPE: DNA
<213> ORGANISM: Homo sapiens

<400> SEQUENCE: 2

| | | | | | |
|---|---|---|---|---|---|
| atggacgggt | ccggggagca | gcccagaggc | gggggcccca | ccagctctga | gcagatcatg | 60 |
| aagacagggg | ccctttttgct | tcagggtttc | atccaggatc | gagcagggcg | aatggggggg | 120 |
| gaggcacccg | agctggccct | ggaccccgtg | cctcaggatg | cgtccaccaa | gaagctgagc | 180 |

```
gagtgtctca agcgcatcgg ggacgaactg gacagtaaca tggagctgca gaggatgatt        240
gccgccgtgg acacagactc cccccgagag gtcttttcc gagtggcagc tgacatgttt         300
tctgacggca acttcaactg gggccgggtt gtcgcccttt tctactttgc cagcaaactg        360
gtgctcaagg ccctgtgcac caaggtgccg gaactgatca gaaccatcat gggctggaca        420
ttggacttcc tccgggagcg gctgttgggc tggatccaag accagggtgg ttgggacggc        480
ctcctctcct actttgggac gcccacgtgg cagaccgtga ccatctttgt ggcgggagtg        540
ctcaccgcct cgctcaccat ctggaagaag atgggctga                               579

<210> SEQ ID NO 3
<211> LENGTH: 619
<212> TYPE: DNA
<213> ORGANISM: Encephalomyocarditis virus

<400> SEQUENCE: 3
tctagataat acgactcact atagggcgaa ttccccctct cctcccccc cccctaacgt          60 tactggccga agccgcttgg aataaggccg gtgtgcgttt gtctatatgt tattttccac        120
catattgccg tcttttggca atgtgagggc ccggaaacct ggccctgtct tcttgacgag        180
cattcctagg ggtctttccc ctctcgccaa aggaatgcaa ggtctgttga atgtcgtgaa        240
ggaagcagtt cctctggaag cttcttgaag acaaacaacg tctgtagcga ccctttgcag       300
gcagcggaac cccccacctg cgacaggtg cctctgcggc caaaagccag gtgtataaga        360
tacacctgca aaggcggcac aaccccagtg ccacgttgtg agttggaata gttgtggaaa       420
gagtcaaatg gctctcctca agcgtattca acaaggggct gaaggatgcc cagaaggtac       480
cccattgtat gggatctgat ctggggcctc ggtgcacatg ctttacatgt gtttagtcga       540
ggttaaaaaa cgtctaggcc ccccaaccac ggggacgtgg ttttcctttg aaaaacacga       600
ttattatatt gcctctaga                                                    619
```